US008577452B2

(12) United States Patent
Bradley et al.

(10) Patent No.: US 8,577,452 B2
(45) Date of Patent: Nov. 5, 2013

(54) METHOD OF ACQUIRING A PHYSIOLOGICAL RESPONSE

(75) Inventors: Andrew P Bradley, Brisbane (AU); Wayne J Wilson, Brisbane (AU)

(73) Assignee: The University of Queensland, Queensland (AU)

( * ) Notice: Subject to any disclaimer, the term of this patent is extended or adjusted under 35 U.S.C. 154(b) by 1092 days.

(21) Appl. No.: 12/373,502

(22) PCT Filed: Jul. 12, 2007

(86) PCT No.: PCT/AU2007/000969
§ 371 (c)(1),
(2), (4) Date: Sep. 9, 2009

(87) PCT Pub. No.: WO2008/006164
PCT Pub. Date: Jan. 17, 2008

(65) Prior Publication Data
US 2010/0030096 A1    Feb. 4, 2010

(30) Foreign Application Priority Data

Jul. 12, 2006  (AU) .............................. 2006903747

(51) Int. Cl.
*A61B 5/04*  (2006.01)
(52) U.S. Cl.
USPC ......................................... 600/545; 600/544
(58) Field of Classification Search
USPC ............................................... 600/544–545
See application file for complete search history.

(56) References Cited

U.S. PATENT DOCUMENTS

| 4,018,218 A * | 4/1977 | Carlson et al. ................. 600/26 |
| 6,406,438 B1 * | 6/2002 | Thornton ....................... 600/559 |
| 2010/0145222 A1 * | 6/2010 | Brunnett et al. .............. 600/554 |

FOREIGN PATENT DOCUMENTS

| JP | H7-505306 | 6/1995 |
| JP | H8-509827 | 10/1996 |
| JP | 2001-526922 | 12/2001 |
| WO | WO99/32989 | 7/1999 |
| WO | WO01/87147 | 11/2001 |

OTHER PUBLICATIONS

Supplementary European Search Report from corresponding European Application No. 07784638.4 dated May 17, 2010.
Delgado, Rafael et al, "Deconvolution of evoked responses obtained at high stimulus rates," J. Acoust. Soc. Am. 115, Mar. 2004, pp. 1242-1251.
Rasmussen et al. *Neonatal Hearing Screening using Otoacoustic Emissions Elicited by Maximum Length Sequences*, British Journal of Audiology, 1998, vol. 32, pp. 355-366.

\* cited by examiner

*Primary Examiner* — Michael Kahelin
*Assistant Examiner* — Karen Toth
(74) *Attorney, Agent, or Firm* — Workman Nydegger

(57) ABSTRACT

A method for acquiring a physiological response from a test subject, particularly an auditory brainstem response, by presenting a plurality of stimuli, such as a Maximum Length Sequence, detecting electrophysiological signals in response to the stimuli, generating a recover signal based on the stimuli and determining the physiological response from the electrophysiological signals and the recovery signal.

49 Claims, 11 Drawing Sheets

METHOD OF ACQUIRING A PHYSIOLOGICAL RESPONSE

FIELD OF THE INVENTION

The invention relates to assessing response to stimuli in humans and other animals. In particular, although not exclusively, the invention relates to a method for acquiring and reconstructing an electrophysiological recording of an auditory brainstem response (ABR).

BACKGROUND TO THE INVENTION

The assessment of response to stimuli is an important aspect of medical screening. Stimuli response assessment is useful for diagnosing problems with vision, feeling and hearing. Early detection of hearing difficulties is considered to be a particularly important problem. In the developed world around 20,000 infants each year are born with a significant hearing impairment. Early detection and treatment of such impairments are essential for the age-appropriate development of speech, language and cognitive ability. Therefore, most countries have initiated universal neonatal hearing screening (UNHS) programs. However, the costs of running these programs are considerable, especially in regional and remote areas. The costs associated with running a UNHS program depend on a wide variety of issues, but screening test time and referral rates are two factors that have a significant effect on program cost. Specifically, it can be shown that both halving screening times and referral rates produces more than a 20% reduction in annual costs of running a UNHS program.

There are primarily two types of devices used for neonatal hearing screening: automated auditory brainstem response (A-ABR); and transient evoked otoacoustic emission (TEOAE). A-ABR devices use earphones and surface electrodes to measure the brainstem's response to an acoustic stimulus near the hearing threshold, and then determine whether the response is an ABR waveform or random background noise.

A typical ABR waveform shows up to seven positive peaks in the first 12-15 ms post stimulus. These peaks have been shown to relate to synchronous neural activity along the auditory neural pathway from the $VIII^{th}$ cranial nerve, the auditory brainstem, thalamus and thalamocortical radiations. Conventionally, ABR peaks are labelled, in latency order, using the roman numerals I to VII. Peak I typically occurs at around 2 ms with all subsequent waves following at intervals of around 1 ms. The latencies of waves I, III and V are commonly the most reliably measured with most clinicians simply identifying these peaks and then comparing their latencies to normative data matched for stimulus type, intensity and rate etc.

TEOAE devices use earphones and a microphone to measure the cochlea's response to an acoustic stimulus, and then determine whether the response is an otoacoustic emission or random background noise. Both the A-ABR and the TEOAE devices produce a pass/refer decision based on the presence or absence of a response from the brainstem (A-ABR) or the cochlea (TEOAE).

An advantage of the A-ABR is that it tests the integrity of the outer, middle and inner ear (indirectly) and the auditory nerve and brainstem (directly); whereas the TEOAE tests only the integrity of the outer and middle ear (indirectly) and the inner ear (directly). An advantage of the TEOAE is that it can be completed faster and costs less to perform. A disadvantage of the TEOAE is that it results in a higher rate of false alarms, causing significantly higher referral rates (approximately twice that of the A-ABR). These higher referral rates result in significantly increased follow-up costs and significantly higher levels of (often needless) parental anxiety.

There are two significant limitations that impede clinical use of the A-ABR as a neonatal hearing screening device:
1. The acquisition of the ABR is subject to high levels of noise interference from both external noise sources and the neonate being tested. Therefore, data acquisition times for the near-threshold ABR waveforms required for UNHS are typically around 5 minutes. Furthermore, in less favourable acquisition conditions, say with an unsettled neonate, acquisition times regularly extend to 20 minutes, after which testing is typically aborted until another time. That is not an ideal outcome as it adds to parental anxiety and can result in the neonate subsequently going home untested.
2. It is normal practice with the A-ABR to test for the presence or absence of a response at only one, near-threshold, stimulus intensity (typically 35 dB nHL) (which practice is a direct result of the lengthy ABR acquisition times.) Although a more thorough and accurate ABR test could be performed utilising multiple stimulus intensities, both above and below the hearing threshold, generally that is done only during diagnostic evaluation due to the prohibitively long test times.

The ABR waveform used for clinical interpretation is the average response waveform after the presentation of between 1000 and 4000 stimuli and is known as the ensemble average. The reason why an ensemble average is required is because of the poor signal-to-noise ratio (SNR) obtained from the presentation of any one stimulus. The poor SNR is a direct result of the evoked potential being measured in the presence of other acoustic and electrical sources, which are considered to be noise, including:

Ongoing neural activity in the brain, as measured by an electroencephalogram;
Involuntary muscular activity, such as eye and head movement;
Electromagnetic interference, such as that radiated by mains wiring and electrical equipment in the vicinity, e.g., power supplies, lights, and switches; and
Acoustic interference, such as ambient or background noise.

Ensemble averaging is effective at reducing noise from the above four sources, with the possible exception of muscle artefacts, as the sources are all zero mean and unsynchronised to the auditory stimulus. Ensemble averaging simply assumes that the signal is deterministic and synchronised to the stimulus, whilst the noise is zero mean and not synchronised to the stimulus. Experience shows that these assumptions are generally valid.

The most commonly used stimulus in A-ABR devices is a 100 μs positive or negative going impulse, known as a broadband "click." If the outer ear to auditory brainstem behaved as a linear system (which it generally does not) then such click stimulus would directly measure the impulse response of this system. However, it is well known that using an impulse, or in this case a periodic impulse train, is not the most efficient method to estimate the impulse response of a linear system. Other broadband stimuli such as white noise, stepped-frequencies or chirp signals enable increased signal power to be injected into the system and hence increase the SNR at the output. This response then can be directly related to the required impulse response via cross-correlation and/or Fourier analysis. One such stimulus, consisting of a pseudo-random impulse train, often referred to as a maximum length sequence (MLS), has been proposed in the prior art. The primary advantage of the MLS is that it allows for clicks to be presented before the response to the previous click has fully dissipated. This allows for an effective increase in pulse repetition frequency, also known as inter-stimulus interval (ISI) and hence results in reduced test times.

However, there are a number of issues that have impeded the wide-spread adoption of MLS stimuli:

1. The irregular ISI of the MLS leads to increased response variability, and so the ABR is not optimally reconstructed and waveforms often have (presumably contaminated) non-standard morphology;
2. Decreasing the ISI (that is, increasing the rate of stimulus presentation) results in reduced ABR amplitudes. If the increase in rate does not compensate for the decrease in ABR amplitude, then the SNR will actually worsen.

The conventional MLS reconstruction algorithm is based on cross-correlating the response evoked by the MLS with the MLS itself. MLSs are defined so that their auto-correlation is a unit impulse and so this process effectively estimates the impulse response of the system, which ideally results in the acquired ABR. However, this reconstruction process is only optimal for responses generated by systems that are approximately linear and time-invariant. But both ABR amplitude and latency vary significantly with ISI, so conventional linear reconstruction algorithms are sub-optimal.

The application of MLS to the acquisition of the ABR was first described in 1982 by Eysholdt and Schreiner [Eysholt U. and Schreiner, C. H. R. (1982) Maximum length sequences—a fast method for measuring brain-stem-evoked potentials. Audiol, 21, 242-250]. The method of ABR reconstruction described by Eysholdt and Schreiner is based on a computationally efficient matrix inversion technique. However this method is only optimal when applied to the reconstruction of MLS signals acquired from a linear time-invariant system. Reference may also be had to U.S. Pat. No. 5,734,827 by Thornton et. al. which describes a memory efficient implementation of the conventional linear MLS reconstruction algorithm where response reconstruction is performed as the data is acquired.

Although the conventional (linear) MLS reconstruction technique has been used extensively since then, a number of alternative reconstruction techniques have been proposed that attempt to overcome the short comings of this method. For example, Van Veen and Lasky [Van Veen B. D., Lasky R. E. (1994) A Framework for Assessing the Relative Efficiency of Stimulus Sequences in Evoked Response Measurements. J Acoust Soc Am 96(4), 2235-2243] describe a framework for assessing the efficiency of MLS reconstruction sequences. They describe a method where they can select recovery sequences that maximise the signal-to-noise ratio (SNR) of the reconstructed ABR waveforms. However, in their work they limit their analysis to MLS responses that consist of a sum of scaled and shifted versions of the desired ABR impulse response, thereby ignoring the implicit variations in ABR latency.

In a more recent attempt to improve upon the conventional MLS acquisition and reconstruction techniques Jewett et al [Jewett D. L., Caplovitz G., Baird W., Trumpis M., Olson M. P. and Larson-Prior L. J. (2004) The use of QSD (Q-Sequence Deconvolution) to Recover Superposed, Transient Evoked-Responses, Clin. Neuro. 115(12), 2754-2775.] describe a q-sequence deconvolution (QSD) method that utilises stimulus sequences with minimal ISI variation (so called 'quasi-periodic' sequences) so as to minimise ABR latency variation. However, a major limitation of this approach is that it relies on a deconvolution operation which is conventionally implemented as a division operation in the Fourier domain. It is well known that division in frequency domain can significantly amplify noise in the signal as a result of any Fourier coefficients smaller than one. Therefore, they propose a computationally expensive, iterative procedure that attempts to find a q-sequence that meets certain pre-specified time and frequency domain constraints (including exclusion of Fourier magnitudes less than 1). It should be noted that the existence of a q-sequence that meets a given set of constraints is not assured and hence the QSD method has limited applicability.

The application of MLS to MLR (middle latency response) is described in Bell et al [Bell S. L., Allen, R and Lutman M. E. (2002) Optimizing the acquisition time of the middle latency response using maximum length sequences and chirps. J Acoust Soc Am 112(5), 2065-2073]. Bell describes varying the minimum ISI between 250 µs and 2.5 ms and measuring the associated wave (peak to trough) amplitudes and latencies. Whilst Bell reports only small (statistically insignificant) changes in observed wave latencies, there is a clear ISI-amplitude non-linearity as demonstrated through a significant decrease in wave amplitude as stimulus rate increases.

The application to MLS in TEOAE is described in U.S. Pat. No. 5,546,956 by Thornton. The preferred embodiment of the invention describes an acoustic stimulus that is measured by an aural probe inserted in the subject's ear canal. This probe consists of a microphone, with associated signal amplification, that detects the sound returned from the subject's cochlear in response to the auditory stimulus. In this work the minimum ISI is varied between 200 µs and 25 msec and the associated OAE responses show a clear decrease in amplitude as ISI is decreased. However, as the OAE is a response primarily from the mechanical, rather than neurological, portions of the middle and inner ear, there is only minimal change in latency as ISI is varied.

There is therefore a need for an improved method for acquiring a physiological response, which method overcomes many of the above described disadvantages of the prior art.

OBJECTS OF THE INVENTION

Therefore an object of the present invention is to overcome or at least alleviate one or more of the above limitations including providing a method for acquiring an auditory brainstem response.

SUMMARY OF THE INVENTION

Accordingly, in one form, the present invention is a method for acquiring a physiological response, comprising the steps of: presenting to a test subject a plurality of stimuli with variable inter-stimulus intervals; detecting an electrophysiological signal from the test subject in response to the stimuli; generating a recovery signal based on the stimuli, where an amplitude and latency of the recovery signal are modified according to the inter-stimulus intervals of the stimuli; and determining a physiological response signal using both the electrophysiological signal and the recovery signal.

Suitably the stimuli are auditory stimuli and the physiological response is an auditory brainstem response (ABR).

Optionally, more than 1,000 auditory stimuli are presented to the test subject's ear.

Optionally, the auditory stimuli can be broad band clicks, tone bursts, noise bursts, chirp stimuli, or other types of stimuli.

Optionally, generating a recovery signal based on the auditory stimuli comprises application of a comb filter.

Optionally, the method is performed using an automated auditory brainstem response (A-ABR) device.

Optionally, the method can be applied to both ears of a single test subject simultaneously.

Optionally, the test subject is a human neonate.

The present invention therefore enables acquisition of an improved ABR. Embodiments of the present invention enable ABR waveforms to be acquired in a significantly reduced time compared to the prior art thus improving the effectiveness of A-ABR devices in various ways. For example, according to a method of the present invention, a single stimulus intensity can be tested in significantly less time than is required according to prior art techniques, allowing for more successful testing in difficult environments, such as where the test subject is a fidgety neonate or where there is significant background noise. Also, embodiments of the present invention enable multiple stimulus intensities to be tested during a test period that is comparable in length to prior art test periods, but that results in increased test accuracy and reliability.

Further features and advantages of the present invention will become apparent from the following detailed description.

BRIEF DESCRIPTION OF THE DRAWINGS

To assist in understanding the invention and to enable a person skilled in the art to put the invention into practical effect, preferred embodiments of the invention will be described by way of example only with reference to the accompanying drawings, in which.

DETAILED DESCRIPTION OF THE INVENTION

Figure 1:
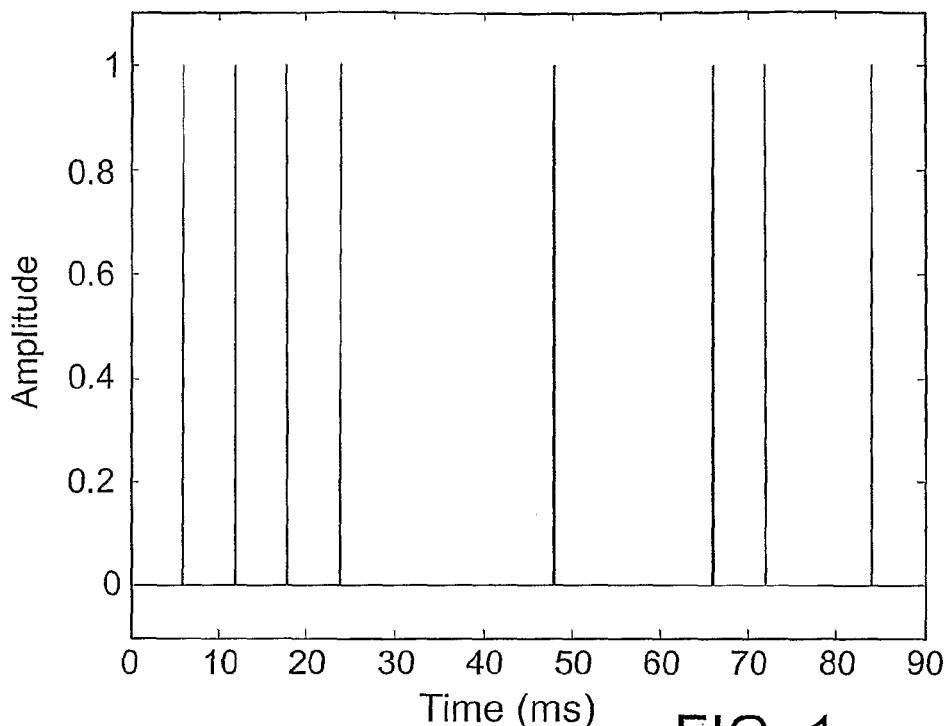
FIG. 1 is a graph of amplitude v. time illustrating an MLS, according to an embodiment of the present invention.

Embodiments of the present invention reside primarily in method steps for acquiring an auditory brainstem response. Accordingly, the method steps have been illustrated in concise schematic form in the drawings, showing only those specific details that are necessary for understanding the embodiments of the present invention, but so as not to obscure the disclosure with excessive detail that will be readily apparent to those of ordinary skill in the art having the benefit of the present description.

In this specification, adjectives such as first and second, left and right, and the like may be used solely to distinguish one element or action from another element or action without necessarily requiring or implying any actual such relationship or order. Words such as "comprises" or "includes" are intended to define a non-exclusive inclusion, such that a process, method, article, or apparatus that comprises a list of elements does not include only those elements but may include other elements not expressly listed, including elements that are inherent to such a process, method, article, or apparatus.

As discussed above, conventional MLS reconstruction algorithms are based on cross-correlating a response evoked by an MLS with the MLS itself. MLSs are defined so that their auto-correlation is a unit impulse, thus this process effectively estimates the impulse response of the system, which ideally results in the acquired ABR. However, such a reconstruction process is only optimal for responses generated by systems that are approximately linear and time-invariant. In real world environments, both ABR amplitude and latency vary significantly with ISI. Therefore, conventional linear reconstruction algorithms are sub-optimal.

According to an embodiment of the present invention, a recovery signal is generated that compensates for the variability in latency and amplitude of a response due to the variable ISIs. Aspects of the present invention thus provide an improved method of acquiring ABR waveforms, which enables an A-ABR device to be operated as quickly and easily as a TEOAE device, but with an accuracy that is equivalent to, or superior to, conventional A-ABR devices.

For clarity, the present detailed description relates to a specific embodiment of the present invention where specific values are specified for certain free parameters. As will be understood by those skilled in the art, other parameter settings can be selected and utilised within the scope of the present invention. However, the present detailed description is based on the following specific parameter settings:

Sampling frequency (Fs) of both analogue to digital (A2D) and digital to analogue (D2A) converters are set to 40 kHz. This relates to a sampling period (Ts=1/Fs) of 25 microseconds. As is known in the prior art, it is not a restriction on the invention to run both the D2A and A2D at the same frequency, although it is often preferable, in terms of ease of implementation, to run them at integer multiples of each other.

Order (O) of the MLS is set to 4 for the purpose of description, in practice an MLS of order 6 is likely to be employed. Order 4 produces a bipolar MLS sequence of length $L=2^O-1=15$. This results in a unipolar MLS consisting of eight 1's (clicks) and seven 0's (silences). In this disclosure we utilise "repeatable" sequences that are generated from an initialisation sequence of all ones.

Stimulus pulse width (Pw) is set to 100 microseconds (µs). At the chosen D2A frequency this relates to four sample periods.

Minimum inter-stimulus interval (MISI) is set to 6 milliseconds (ms).

During data acquisition a differential mode biomedical amplifier is utilised with the following settings: gain=100,000; high-pass cut-off frequency=100 Hz; low-pass cut-off frequency=5 kHz; AC coupled; No 50 Hz Notch filter.

Referring to FIG. 1, a graph of amplitude v. time illustrates an MLS, according to an embodiment of the present invention. Maximum length sequences have been used extensively in the prior art for transfer function and/or impulse response measurement of linear systems. The essence of such techniques is to apply an analogue version of an MLS to a system under test, sample the resulting response and then cross-correlate this response with the original MLS or a sequence derived from it.

An MLS can be easily generated using shift registers as known in the prior art. Initially, a bipolar MLS is generated such as the following:
{−1; −1; −1; −1; 1; 1; 1; −1; 1; 1; −1; −1; 1; −1; 1}
that is then converted to a unipolar sequence according to the formula:

$$y=-0.5(x-1),\quad\text{Eq. 1}$$

resulting in the following sequence:
{1; 1; 1; 1; 0; 0; 0; 1; 0; 0; 1; 1; 0; 1; 0}

Next, each stimulus (1) and silence (0) in the sequence must be interpolated to the required stimulus pulse width. The number of samples required for the stimulus pulse width (Npw) is calculated using:

$$Npw=\text{round}(Pw/Ts)=4.\quad\text{Eq. 2}$$

Round( ) indicates rounding to the closest integer. This is then used to calculate the number of additional zero samples (Nz) that must be inserted into the sequence to achieve the required minimum inter-stimulus interval (MISI) of 6 ms using:

$$Nz=\text{floor}(MISI*Fs/Npw)=60.\quad\text{Eq. 3}$$

Floor( ) indicates rounding to the next smallest integer. The sequence is then modified by inserting 59 (Nz−1) zero samples between each original sample in the sequence and then repeating each sample in this new sequence 3 (Npw−1) times. In this way, a complete stimulus sequence of overall length Ls=3600 (Ls=L*Npw*Nz) samples, or in this case 90 ms, is created. This sequence has 1's in the following sequence indices, all other samples being zero:
{237-240; 477-480; 717-720; 957-960; 1917-1920; 2637-2640; 2877-2880; 3357-3360}

Next, it is necessary to check that the length of the sequence in milliseconds is longer than the expected length of the response to be measured (for an ABR this is typically Tresp=15 ms). If this is not the case it is necessary to either: increase the order of the MLS; increase MISI; increase Pw or a combination thereof until this constraint is met.

The present invention can be implemented using conventional A-ABR hardware apparatus as known in the art. As will be appreciated by those skilled in the art, standard hardware settings used to implement a method of the present invention, such as electrode montages, filter settings, stimulus rates, amplifier gain, resolution, and masking stimuli, can be found in standard prior art text books.

The stimulus sequence generated as described above is presented as an auditory stimulus to a test subject's ear. For example, the sequence is first relayed to a D2A converter sample by sample at the required sampling rate. Next, this (now analogue) signal is relayed to an amplifier and sound transducer connected to the subject's ear. The sound transducer can be, for example, a conventional headphone, insertphone or disposable ear coupler.

The amplifier and transducer combination are conveniently calibrated to present the stimulus at a specified sound pressure level relative to a normalised hearing level. Conventionally, for a single threshold detection acquisition the stimulus intensity is set at a pre-specified level of around 35 dBnHL. However, the test can be repeated at various stimulus intensities both above and below this level in order to more accurately and reliably measure the subject's hearing threshold. According to the present embodiment, the stimulus is presented multiple times to the subject's ear up to a maximum of N=3000, and is presented in a cyclic fashion, that is, as soon as the presentation of a sequence comes to an end, it is repeated again from the start.

In response to the stimulus being presented to the subject's ear, an electrophysiological signal is detected from the test subject. For example, voltages measured at surface electrodes are acquired via a high gain, low-noise, biomedical amplifier, and subsequently sampled by the A2D converter at the specified sampling rate. The biomedical amplifier can be a differential amplifier with active, reference and common (ground) inputs connected to the subject's vertex of scalp (close to Cz), nape of neck and shoulder, respectively. However, other montages such as ipsilateral on mastoid, or on front or back earlobe are also suitable.

Figure 2:
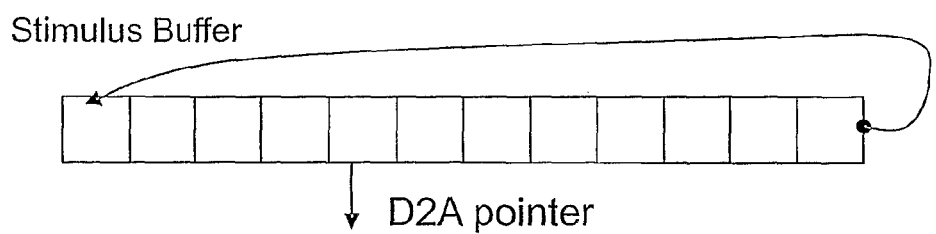
FIG. 2 is a schematic diagram illustrating the use of a cyclical stimulus buffer and a response buffer that stores sequential rows of a response matrix, according to an embodiment of the present invention.
Figure 2:
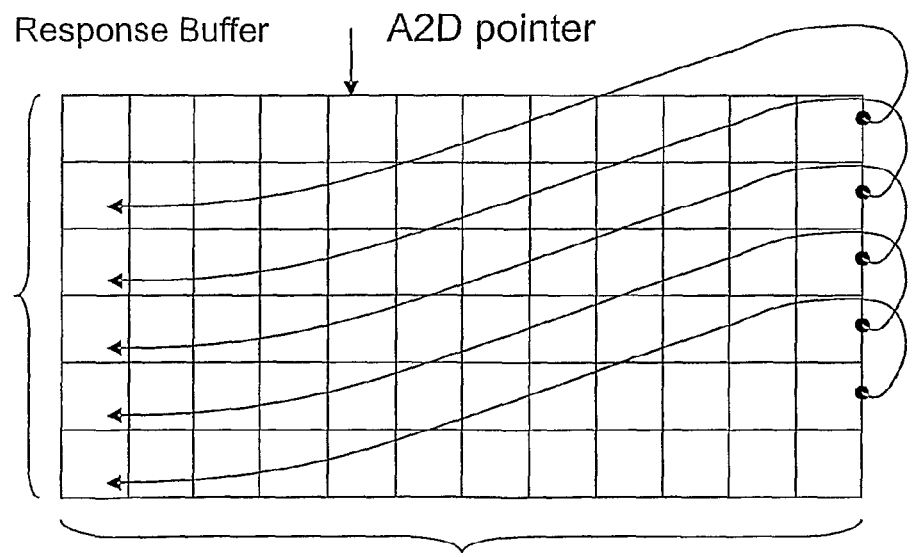

Referring to FIG. 2, a schematic diagram illustrates the use of a cyclical stimulus buffer and a response buffer that stores sequential rows of a response matrix, according to an embodiment of the present invention. As the response to each presentation of the stimulus is acquired it is relayed from the A2D converter and stored in sequential rows of a response matrix with N rows and Ls columns.

A recovery sequence is generated from the stimulus sequence described above as follows. All non-zero samples adjacent to the central stimulus sample are set to zero. The position of the central stimulus sample (Pc) is calculated from the pulse width using Pc=ceil(Pw/2). Ceil( ) indicates rounding to the next largest integer. This results in a sequence that has eight 1's in the following indices:
{239; 479; 719; 959; 1919; 2639; 2879; 3359}
The average inter-stimulus interval (AISI) is calculated based on the length of the sequence (Ls=3600) and the sampling frequency (Fs), giving:

$$AISI=(Ls-1)/Fs=11.247\text{ ms}.\quad\text{Eq. 4}$$

AISI also can be approximated by twice the minimum inter-stimulus interval (2*MISI). Next, the average latency and amplitude of the primary ABR wave (normally peak V, as this is often the only discernable peak near-threshold) is calculated from known functional relationships estimating expected wave latency (Tv) and amplitude (Av) directly from ISI, that is:

$$Tv=\text{WaveAmp(ISI) and } Av=\text{WaveLate(ISI)}. \quad \text{Eq. 5}$$

Figure 3:
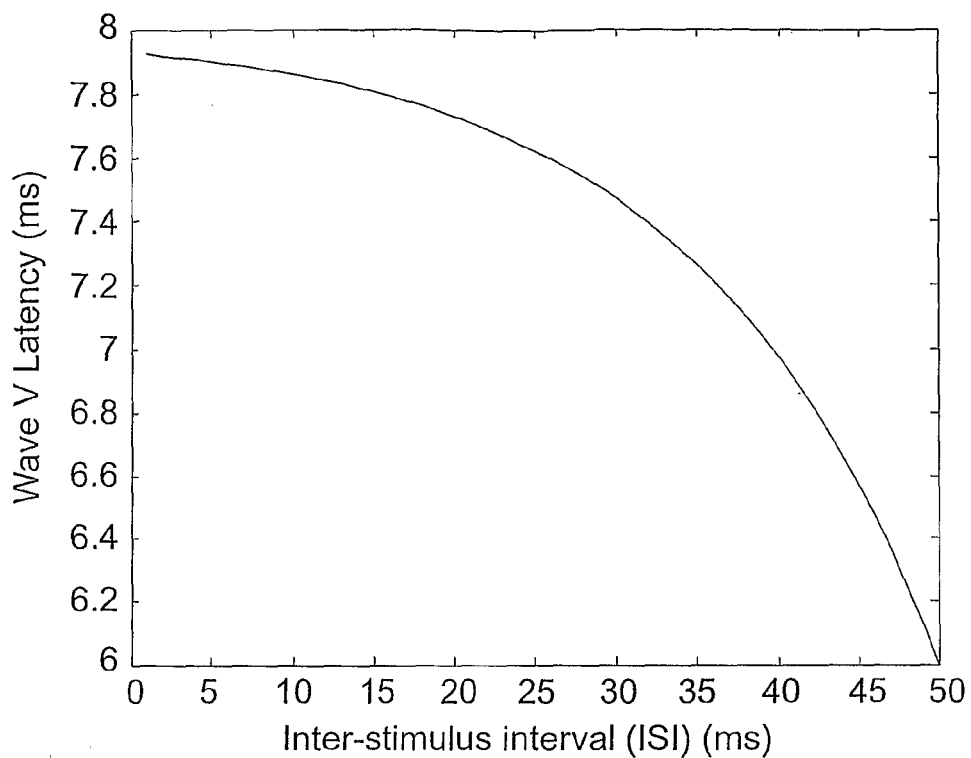
FIG. 3 is a graph illustrating a typical functional relationship between wave latency and ISI, according to an embodiment of the present invention.

Referring to FIG. 3, a graph illustrates a typical functional relationship between wave latency and ISI, according to an embodiment of the present invention.

Figure 4:
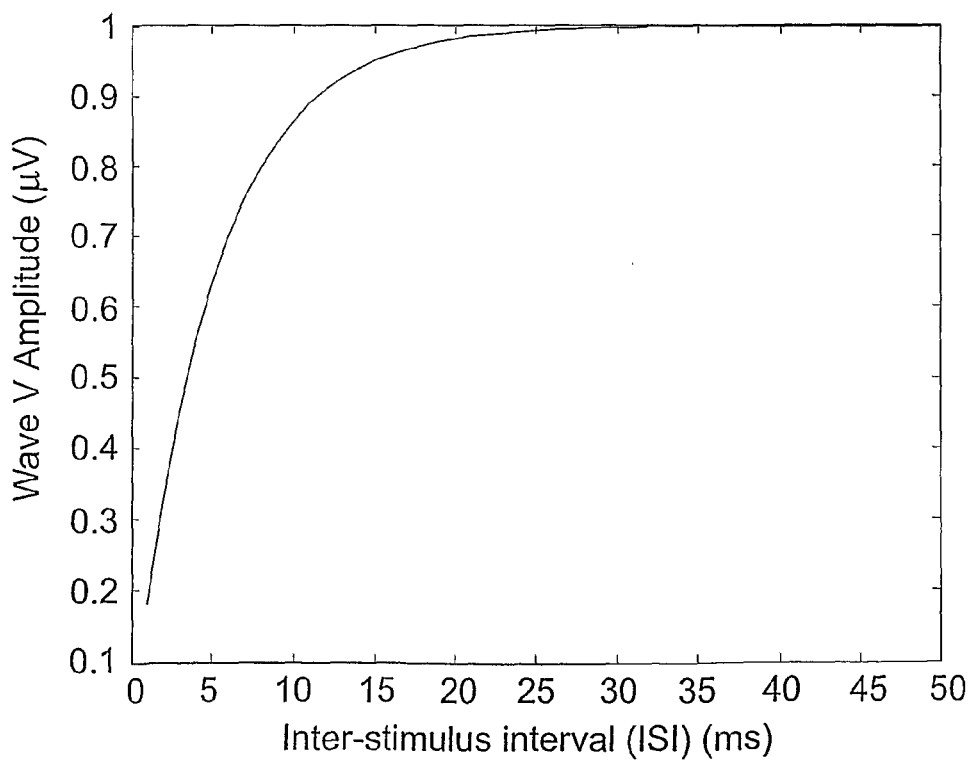
FIG. 4 is a graph illustrating a typical functional relationship between wave amplitude and ISI, according to an embodiment of the present invention.

Referring to FIG. 4, a graph illustrates a typical functional relationship between wave amplitude and ISI, according to an embodiment of the present invention.

The functional relationships illustrated in FIGS. 3 and 4 can be estimated from experimental data. That is, the latency and amplitude of wave V can be measured for a set of subjects (more than 10), with known good hearing, who are of similar age to the subjects to be tested (e.g., neonates). These measurements are taken over the desired range of stimulus amplitudes (typically, from 20 to 50 dBnHL) and periodic inter-stimulus intervals (typically, from around 50 ms to at least 10 ms). Mathematical functions are then fitted to the measured amplitudes and latencies at each inter-stimulus interval. The mathematical form of this relationship can be, for example, linear, piece-wise linear, polynomial, exponential, logarithmic or combinations thereof Various methods are known in the prior art for fitting such functions to that type of data (typically in a least squares sense) and hence determining the best set of coefficients that describe the function. Thus, the fitted functions can be used to estimate expected wave latency and amplitude at inter-stimulus intervals that are either: at measured values; between measured values; or beyond (that is, extrapolated from) measured values (e.g. MISI<10 ms as periodic stimuli cannot be presented at a rate greater than this).

The functional relationships are then used to calculate the following:

1. The expected wave V amplitude (AvAmp) and latency (AvLate) for the average inter-stimulus interval (AISI);
2. The interval (in ms) between subsequent stimuli in the sequence is calculated, with the interval for the first stimulus being calculated circularly from the last stimulus in the sequence. For each of the stimuli in the sequence this measures the time since the previous stimulus in the sequence was presented (note, these are all integer multiples of the MISI):
{12; 6; 6; 6; 24; 18; 6; 12};
3. The expected amplitudes (ExAmp) and latencies (ExLate) are calculated for each individual stimulus in the sequence:
ExAmp={7.841; 7.894; 7.894; 7.894; 7.647; 7.763; 7.894; 7.841},
ExLate={0.909; 0.699; 0.699; 0.699; 0.992; 0.973; 0.699; 0.909};
4. The index of each stimulus in the recovery sequence is modified according to:

$$\text{DeltaOffset=round((ExLate-AvLate)}/Ts); \quad \text{Eq. 6}$$

5. The amplitude of each stimulus in the recovery sequence is modified to become:

$$\text{Amp}=(1+(\text{ExAmp}/\text{AvAmp}))/2; \quad \text{Eq. 7}$$

Figure 5:
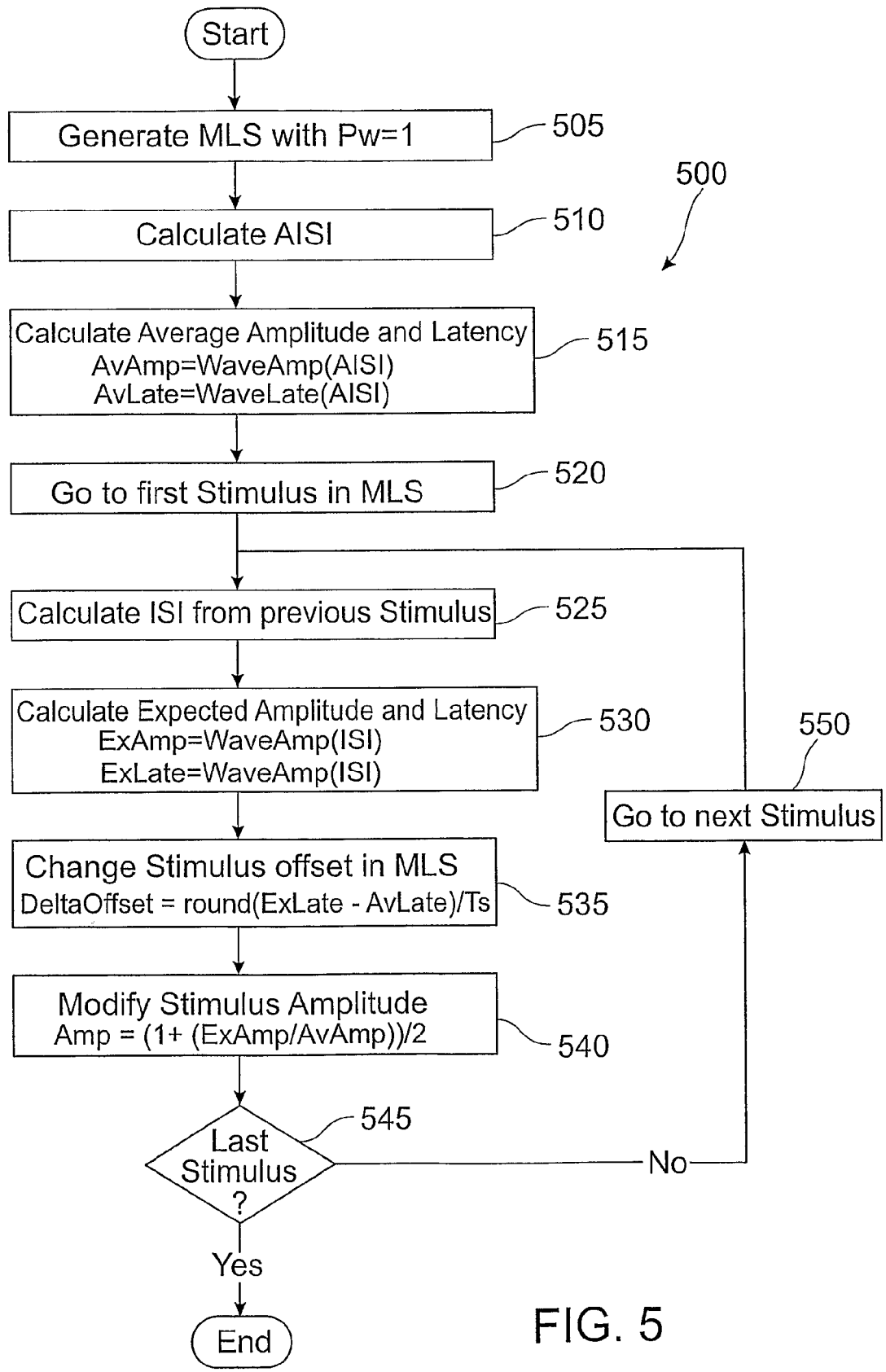
FIG. 5 is a general flow diagram illustrating a method of generating a recovery sequence, according to an embodiment of the present invention.

Referring to FIG. 5, a general flow diagram illustrates a method 500 of generating a recovery sequence as described above, according to an embodiment of the present invention. At step 505 an MLS is generated with Pw=1. At step 510 an AISI is calculated. At step 515 the average amplitude and latency are calculated. At step 520 a stimulus in the MLS is selected and at step 525 the ISI is calculated from the previous corresponding stimulus. At step 530 the expected amplitude and latency are calculated. At step 535 the stimulus offset in the MLS is changed based on equation 6 above. At step 540 the stimulus amplitude is modified based on equation 7 above. At step 545 it is then determined whether the last stimulus has been processed. If not, at step 550 the next stimulus is selected and the method 500 then returns to step 525. When the last stimulus is processed the method 500 ends.

Figure 6A:
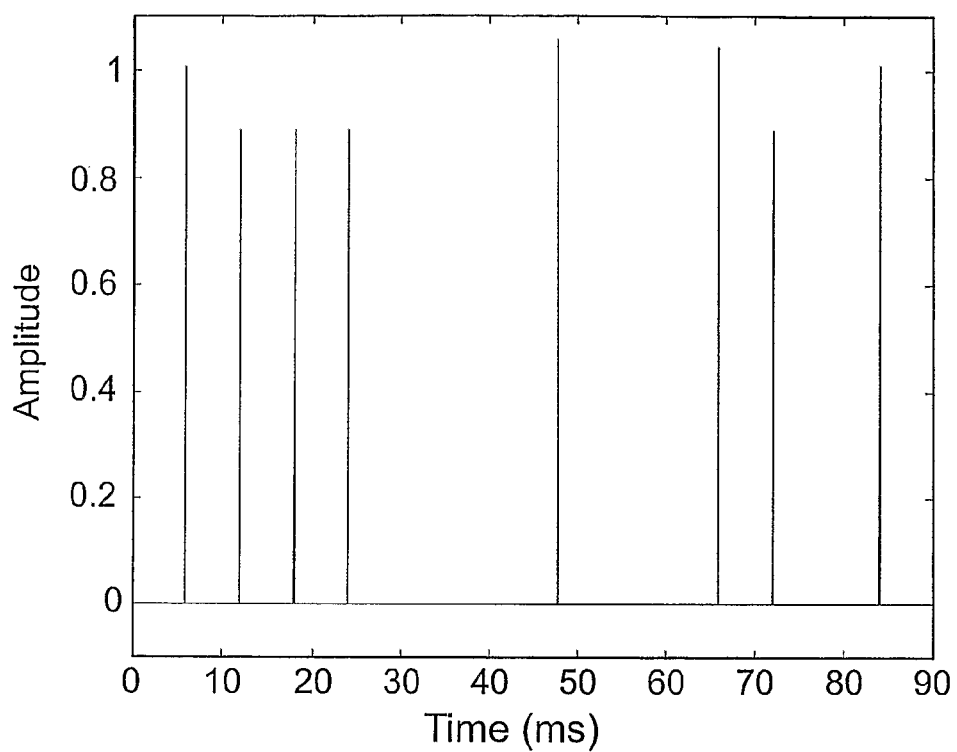
FIG. 6 is a graph of amplitude v. time illustrating a unipolar recovery sequence (FIG. 6a) that results from an embodiment of the present invention and a bipolar recovery sequence (FIG. 6b) that results from another embodiment of the present invention.
Figure 6B:
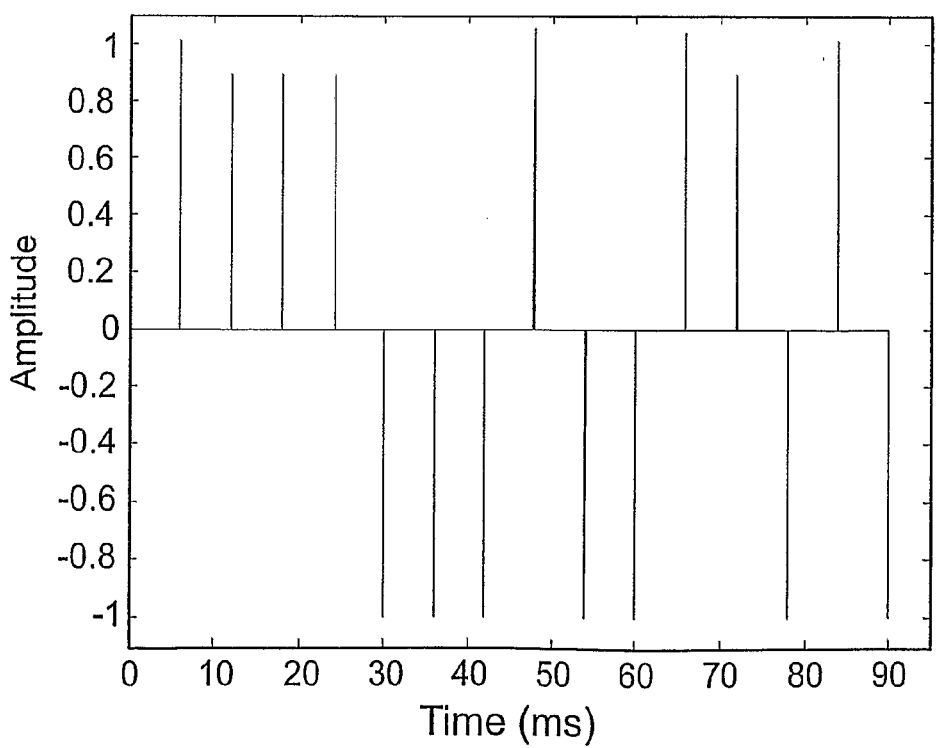

Referring to FIG. 6, a graph of amplitude v. time illustrates a unipolar recovery sequence that results from the above calculations (FIG. 6a), according to an embodiment of the present invention. The sequence has the following non-zero indices:
{239; 481; 721; 961; 1911; 2636; 2881; 3359}
These indices have the following values:
{1.008; 0.891; 0.891; 0.891; 1.054; 1.044; 0.891; 1.008}
It is also possible to generate a bipolar recovery sequence (FIG. 6b), which has the following additional samples set to negative one (−1):
{1199; 1439; 1679; 2159; 2399; 3119; 3599}
According to prior art methods of MLS reconstruction, utilising matrix inversion, the unipolar MLS is used as the stimulus sequence and the bipolar MLS as the recovery sequence.

Figure 7:
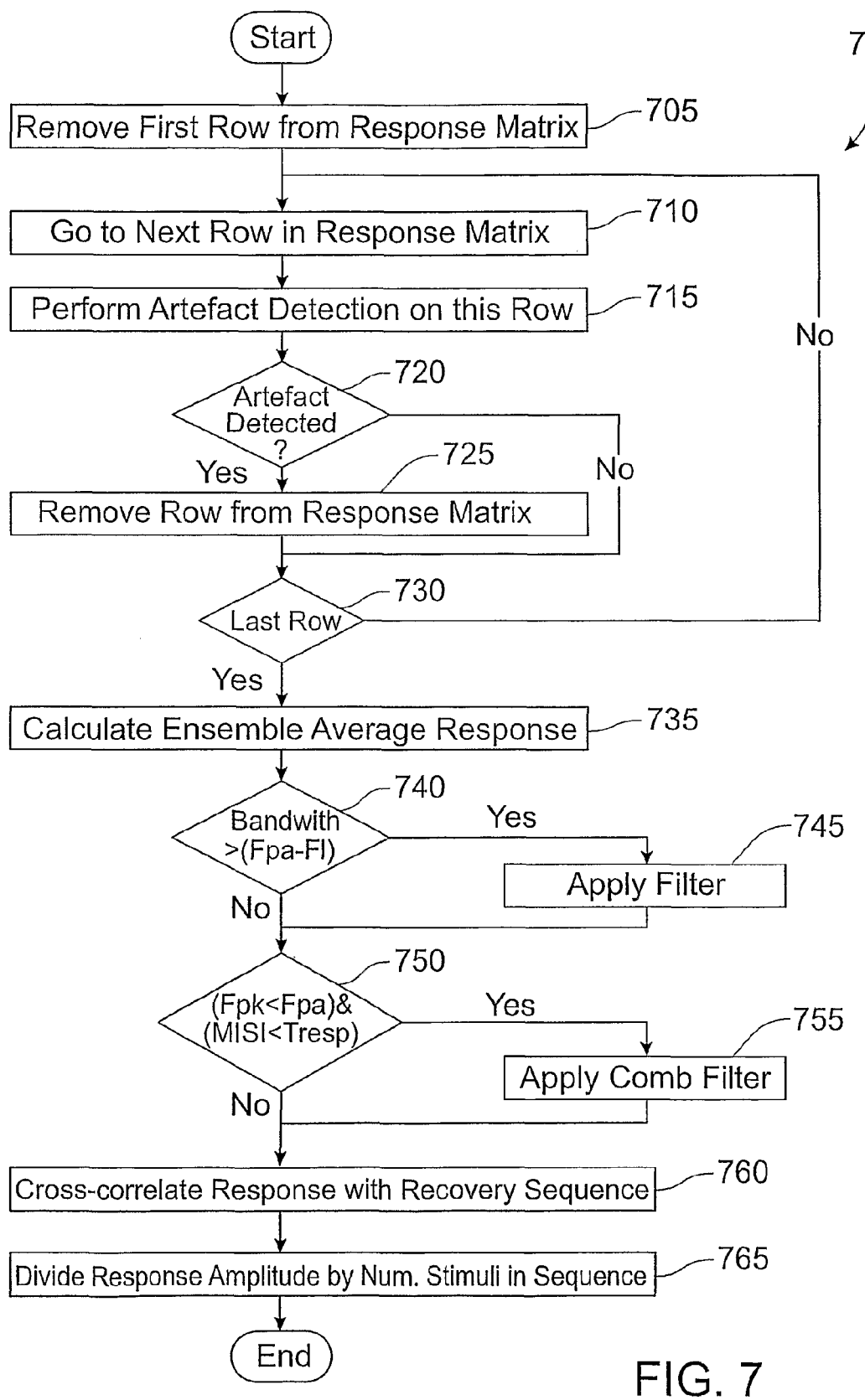
FIG. 7 is a general flow diagram illustrating a method of determining an ABR signal using both an electrophysiological signal and a recovery signal, according to an embodiment of the present invention.

Referring to FIG. 7, a general flow diagram illustrates a method 700 of determining an ABR signal using both an electrophysiological signal and a recovery signal (generated as described above), according to an embodiment of the present invention. The method 700 proceeds as follows: At step 705, the first response (row) is removed from the response matrix. (The first response is contaminated as the system being tested is not yet fully initialised.) At step 710, the method 700 moves to the next row in the response matrix. At step 715, artefact detection is performed on the next row. At step 720 it is determined whether an artefact has been detected. If so, at step 725 the present row is removed. After the present row is removed, or if no artefact is detected, then at step 730 it is determined whether the last row in the response matrix has been processed. If not, the method 700 cycles back to step 710.

According to an embodiment of the present invention, myogenic artefact detection is performed by first filtering the response data with a 200 Hz high-pass filter and then detecting when the resultant signal is greater than a preset threshold. When this threshold is exceeded the response is removed from the response matrix. A number of alternative techniques for detecting primarily high frequency muscle artefacts are known in the prior art. Also, methods are known in the prior art for detecting and removing responses that are contaminated due to ambient acoustic and/or electromagnetic noise.

When the last row in the response matrix is reached according to step 730, the method 700 continues at step 735 where an ensemble average response is calculated. That is, each sample is averaged down the columns of the response matrix to produce a single average response length of Ls=3600 samples (90 ms). At step 740, it is determined whether the bandwidth of the bio-amplifier used to acquire the response data is greater than the expected bandwidth of the response to be recovered (typically, for an ABR, this bandwidth is 30-100 Hz to 1-1.5 kHz). If so, at step 745 a low-pass or band-pass digital filter is applied to the ensemble average response. According to an embodiment of the present invention, the Parks-McClellan optimal equi-ripple finite impulse response (FIR) filter design technique is used to design a low-pass filter with Fpa=1.4 and Fst=1.68 kHz pass-band and stop-band edges, respectively. A reflection boundary extension policy can be used when applying such a filter, and other policies are also known in the prior art.

After the filter is applied at step 745, or if the bandwidth of the bio-amplifier is not greater than the expected bandwidth of the response to be recovered, then at step 750 a determination is made concerning whether to apply a comb filter. The number of samples that were required to be inserted into the recovery sequence to achieve the required MISI is calculated as either: Npw*Nz; or using the minimum number of samples between adjacent stimuli in the initial recovery sequence described above. According to one embodiment, a comb filter is designed that has an attenuation notch every Fpk=Fs/(Npw*Nz)=166.67 Hz, and an infinite impulse response (IIR) with a quality factor (Q) of 20. If Fpk is less than Fpa, and MISI is less than Tresp, then at step 755 the comb filter is applied to the ensemble average response data. According to one embodiment, a reflection boundary extension policy is used when applying the comb filter, but other policies are known in the prior art.

The desired ABR response is recovered at step 760 by cross-correlating the ensemble average response (AvResp) with the recovery sequence (RecMLS) described above. According to an embodiment of the present invention, the cross-correlation is done utilising multiplication in the frequency domain. That is:

ifft(fft(fliplr(RecMLS)).*fft(AvResp)), where .* indicates element wise multiplication, fft( ) indicates the fast Fourier transform of the data vector, ifft( ) the inverse fast Fourier transform, and fliplr( ) indicates a left-right flip of the data vector. Finally, at step 765, the amplitude of this recovered response can be scaled by dividing the amplitude by the number of stimuli in the stimulus sequence (according to the present example, the number of clicks is (L+1)/2=8).

Figure 8:
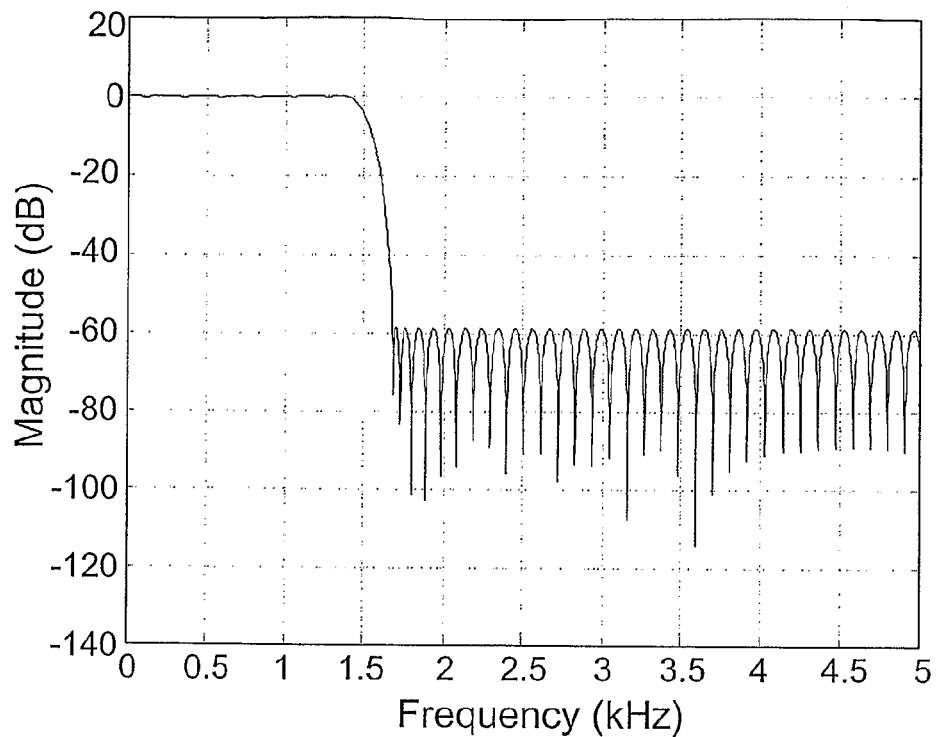
FIG. 8 is a graph of magnitude v. frequency illustrating the magnitude of the frequency response of a bandwidth limiting filter from 0 to 5 kHz, according to an embodiment of the present invention.

Referring to FIG. 8, a graph of magnitude v. frequency illustrates the magnitude of the frequency response of a bandwidth limiting filter from 0 to 5 kHz, according to an embodiment of the present invention.

Figure 9:
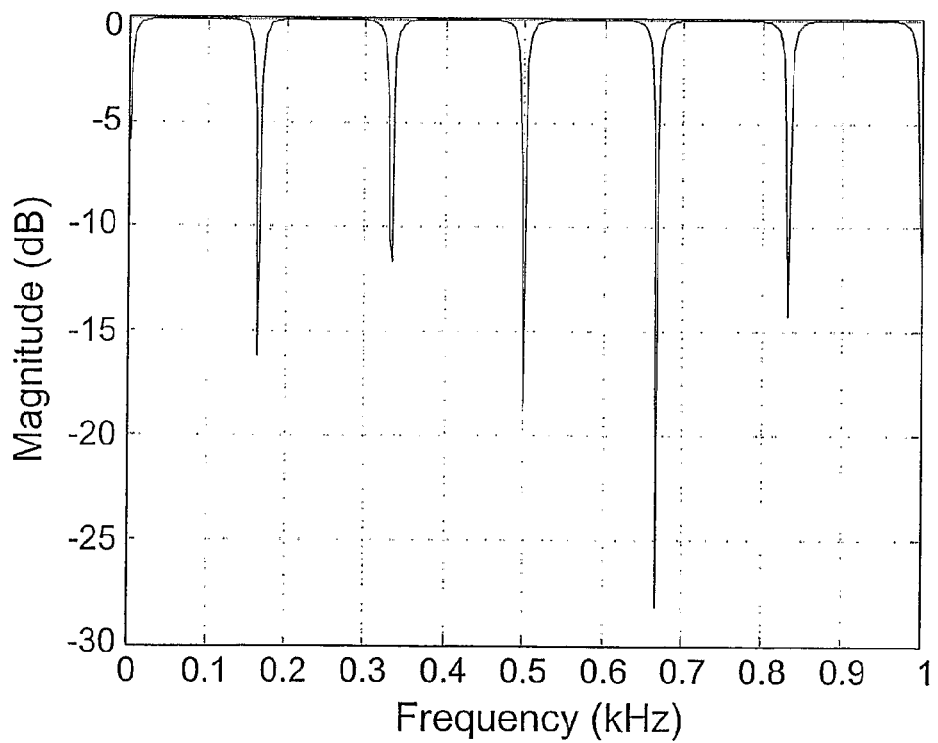
FIG. 9 is a graph of magnitude v. frequency illustrating the magnitude of the frequency response of a comb filter from 0 to 1 kHz, according to an embodiment of the present invention.

Referring to FIG. 9, a graph of magnitude v. frequency illustrates the magnitude of the frequency response of a comb filter from 0 to 1 kHz, according to an embodiment of the present invention. The comb filter is designed for Fs=40 kHz, MISI=6, and Q=20. Those skilled in the art will appreciate that filter design methodologies are known in the art that are capable of designing a single filter with the combined response of the filters described above concerning steps 745 and 755 of the method 700. Although according to the method 700 the filters are applied to the ensemble average response, it will be apparent to those skilled in the art that the filters could equivalently be applied to the recovery sequence.

Figure 10:
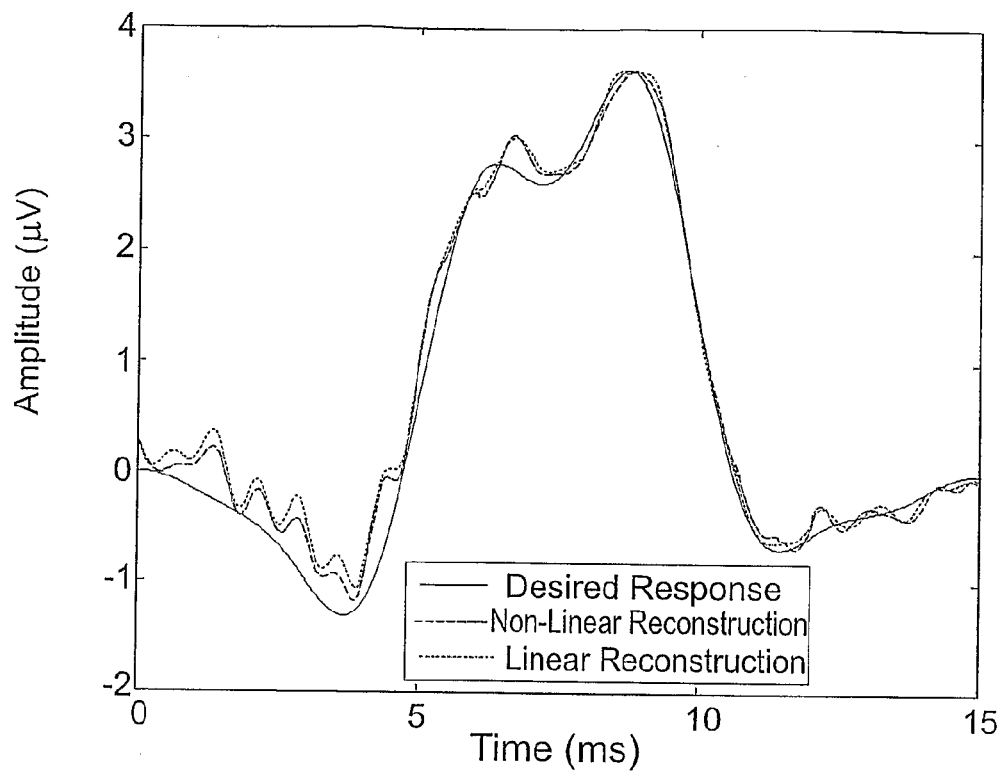
FIG. 10 is a graph of time v. amplitude illustrating a comparison of a desired response and a response reconstruction using a conventional technique according to the prior art (labelled linear reconstruction), and using a method according to an embodiment of the present invention (labelled non-linear reconstruction), where a MISI is set to 6 ms.

Referring to FIG. 10, a graph of amplitude v. time illustrates a comparison of a desired response and a response reconstruction, both using a conventional technique according to the prior art (labelled linear reconstruction), and using a method according to an embodiment of the present invention (labelled non-linear reconstruction). The MISI used to generate the graph of FIG. 10 was set to 6 ms. The root mean square (RMS) difference between the desired response and the reconstructed responses are 0.248 for the linear response and 0.207 for the non-linear response.

Figure 11:
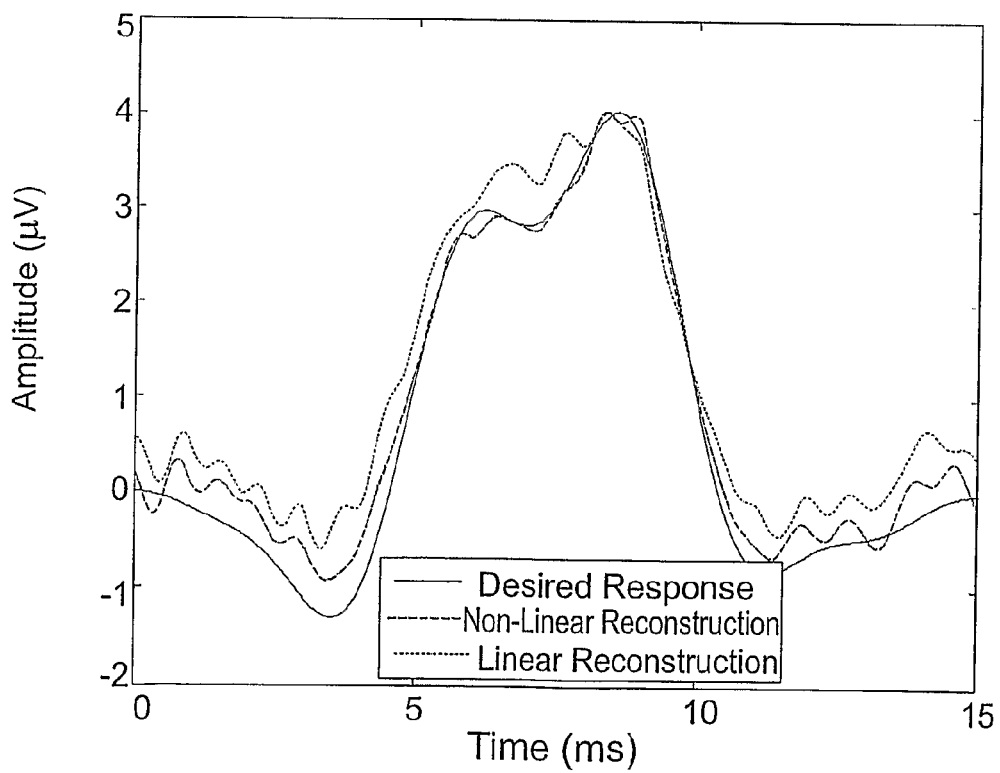
FIG. 11 is a graph similar to that shown in FIG. 10 of time v. amplitude illustrating a comparison of a desired response and a response reconstruction using a conventional technique according to the prior art (labelled linear reconstruction), and using a method according to an embodiment of the present invention (labelled non-linear reconstruction), but where a MISI is set to 12 ms.

Referring to FIG. 11, a graph similar to that shown in FIG. 10 of amplitude v. time illustrates a comparison of a desired response and a response reconstruction, both using a conventional technique according to the prior art (labelled linear reconstruction), and using a method according to an embodiment of the present invention (labelled non-linear reconstruction). However, the MISI used to generate the graph of FIG. 11 was set to 12 ms. The root mean square (RMS) difference between the desired response and the reconstructed responses are 0.554 for the linear response and 0.256 for the non-linear response.

According to still other embodiments of the present invention, it is possible to change the ISI of the stimulus sequence in order to produce responses that appear to have come from a linear system, and therefore improve the performance of a conventional reconstruction algorithm. However, the reconstruction performance can be further improved by using a recovery sequence that reverts to being a conventional MLS recovery sequence, but with amplitudes modified as described above concerning recovery sequence generation. Accordingly, the stimulus generation can be modified by adjusting the indices of the stimuli in the stimulus sequence by an offset calculated as follows:

$$\text{DeltaOffset}=\text{round}((\text{AvLate}-\text{ExLate})/Ts),\qquad\text{Eq. 8}$$

where AvLate is now taken to be the desired wave latency of the response wave, that is, the latency of the response if the system under test were linear. Hence, the presentation time of the stimulus is made earlier if the expected latency is greater (later) than the average latency, and made later if the expected latency is less (earlier) than the average latency.

In a further embodiment of the present invention, other auditory stimuli can be used as an alternative to the conventional broadband click. For example the prior art describes the acquisition of auditory brainstem responses evoked using tone burst and noise burst stimuli, and the acquisition of middle latency responses (MLR) using maximum length sequences of chirp stimuli. In these cases the recovery sequence and process remains the bipolar or unipolar MLS described herein.

In a still further embodiment of the present invention it is possible to gain further reductions in acquisition time by acquiring ABR evoked potentials from both ears of a test subject simultaneously. A simple technique for this is described in the prior art, where circularly shifted versions of the same MLS are used in either ear. The circular shift used introduces a time offset of approximately L/2 into the reconstructed waveforms, and so the responses from the left and right ears can be separated. However, the length of the sequence must then be at least twice the length of the expected response of the system being tested (Tresp) and so the final check at the end of stimulus generation process described above must be modified accordingly. It should also be noted that to acquire responses from both ears at the same time it is convenient to use a centred electrode montage such as the vertical montage described above concerning response acquisition.

Figure 12:
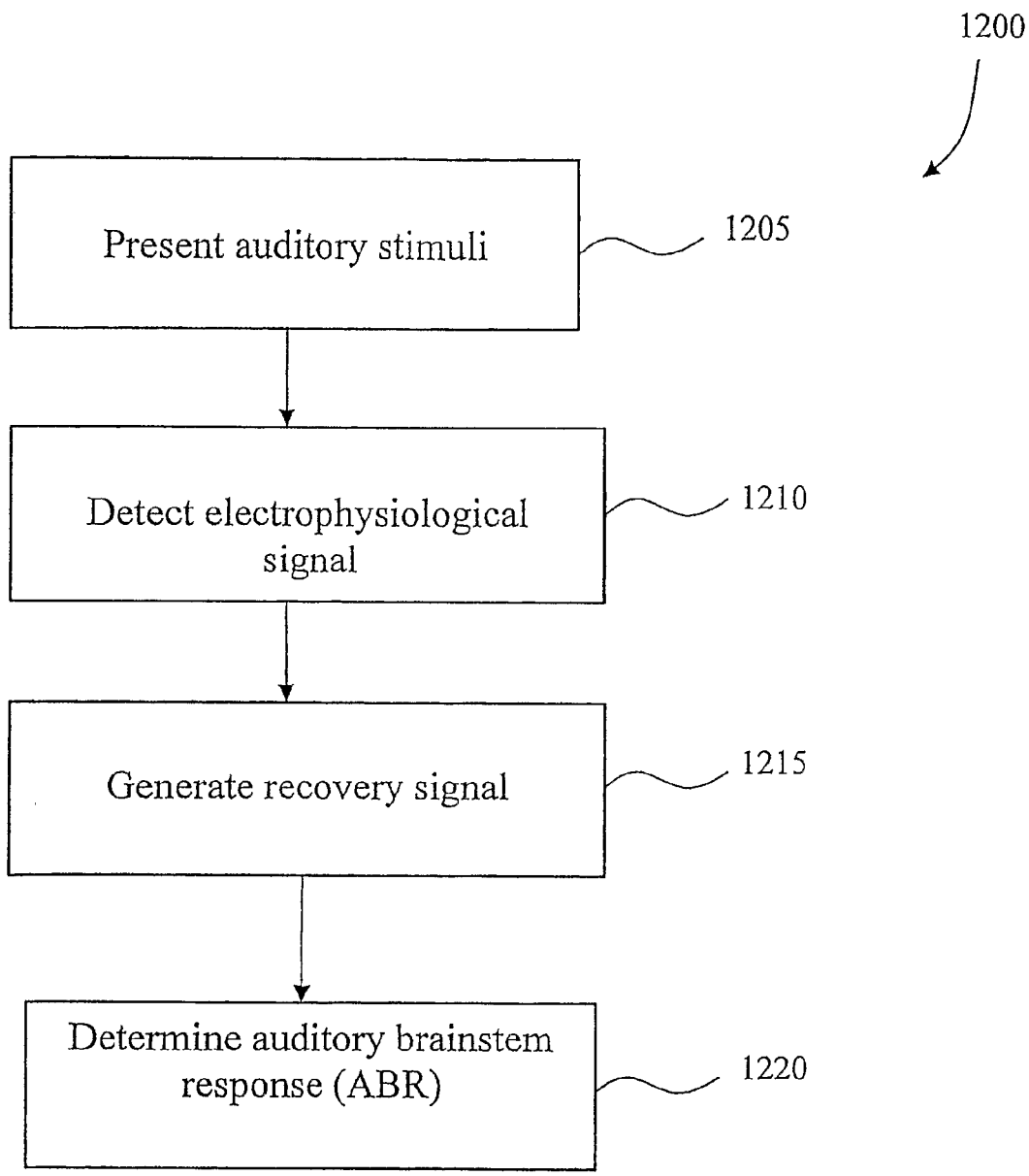
FIG. 12 is a general flow diagram summarizing a method for acquiring an auditory brainstem response, according to an embodiment of the present invention.

Referring to FIG. 12, a general flow diagram summarizes a method 1200 for acquiring an auditory brainstem response, according to an embodiment of the present invention. At step 1205, a plurality of auditory stimuli with variable inter-stimulus intervals are presented to a test subject's ear. At step 1210, an electrophysiological signal is detected from the test subject in response to the auditory stimuli. At step 1215, a recovery signal is generated based on the auditory stimuli, where an amplitude and latency of the recovery signal are modified in proportion to the inter-stimulus intervals of the auditory stimuli. Finally, at step 1220, an auditory brainstem response (ABR) signal is determined using both the electrophysiological signal and the recovery signal.

Figure 13:
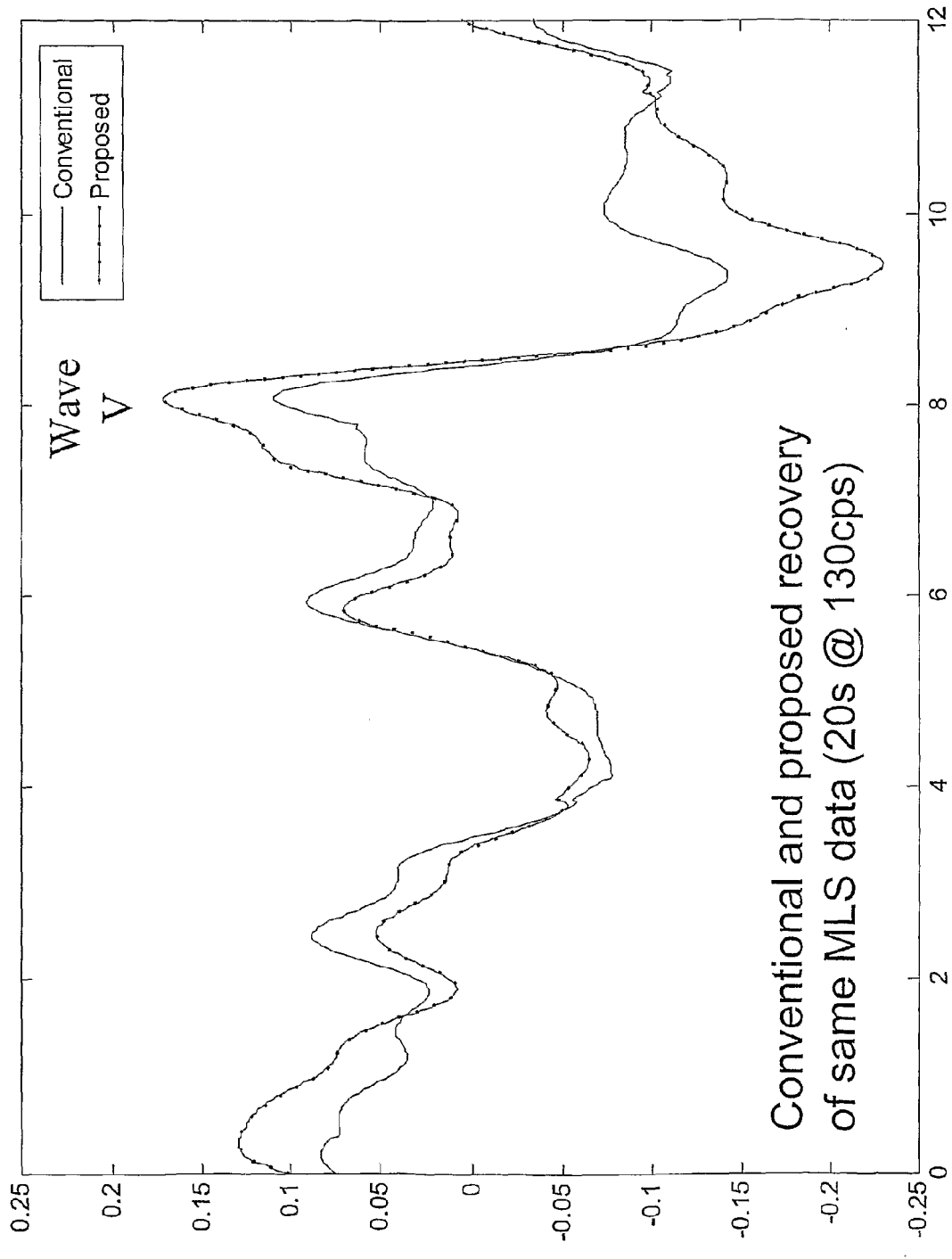
FIG. 13 demonstrates the efficacy of an embodiment of the invention in reconstructing an ABR for an adult subject.

To demonstrate the efficacy of the invention a number of comparisons were made between an ABR reconstructed using the invention and using conventional techniques. FIG. 13 shows an ABR reconstructed from signals acquired from an adult subject at a stimulus intensity of 45 dBnHL. Response data was acquired at an average inter-stimulus interval of 7.52 ms with a 100 μs click stimulus. The reconstruction algorithm of the present invention (labelled proposed) shows a clear increase in the measured peak-to-following-trough amplitude of wave V compared to the conventional (linear) reconstruction algorithm.

Figure 14:
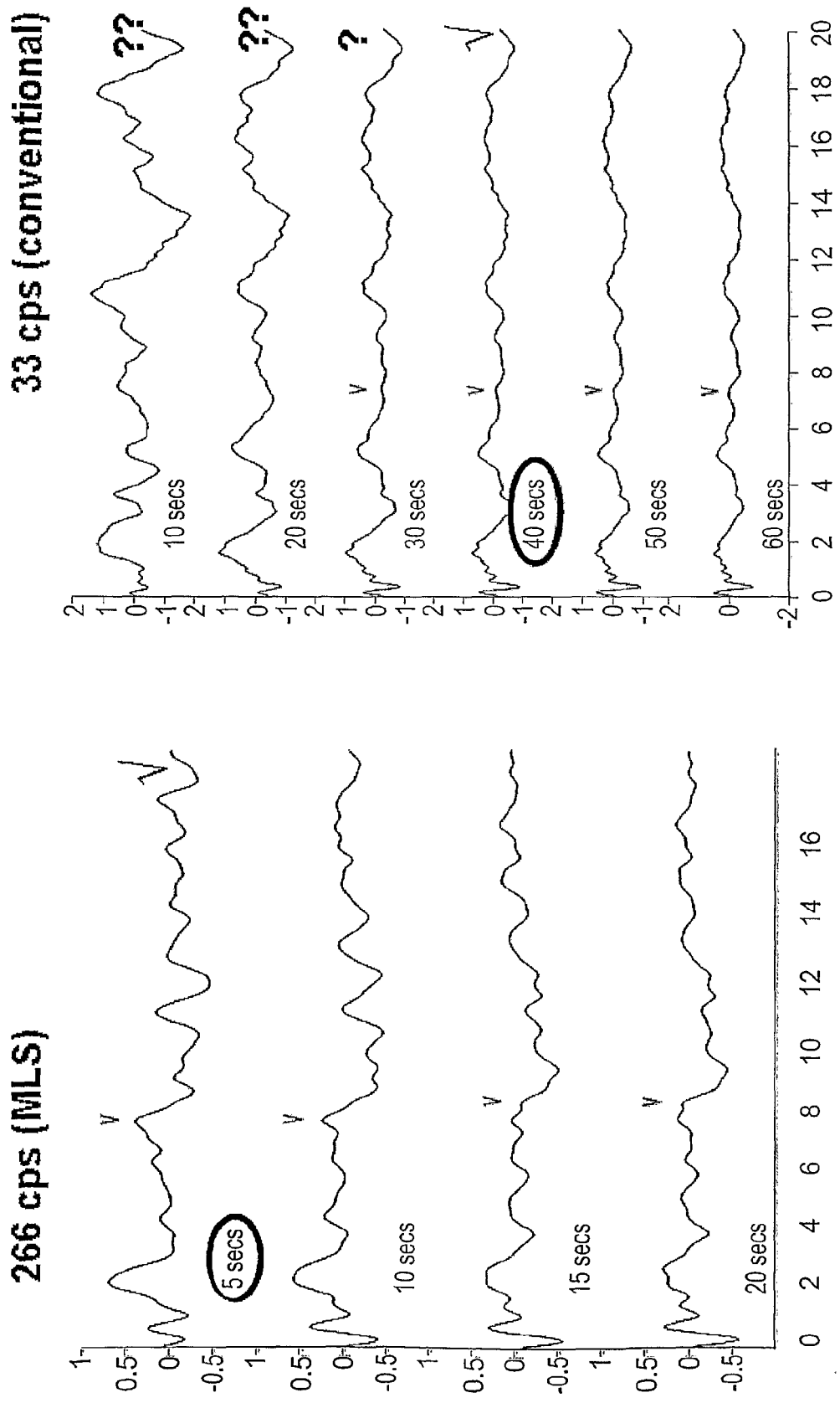
FIG. 14 demonstrates the efficacy of an embodiment of the invention in reconstructing an ABR for a neonate subject.

Comparisons of the time required for an Audiologist to reliably detect the presence of wave V in a neonate were also made. FIG. 14 demonstrates the efficacy of the current invention when reconstructing an ABR acquired from a neonate at a stimulus intensity of 60 dBnHL. Response data was acquired at an average inter-stimulus interval of 3.76 ms with a 100 μs click stimulus. The proposed reconstruction algorithm (left side) shows a clear decrease in the time required for an Audiologist to reliably detect the presence of wave V compared to the conventional periodic click stimuli presented at a (fixed) 30.3 ms inter-stimulus interval (5 seconds compared to 40 seconds).

Figure 15:
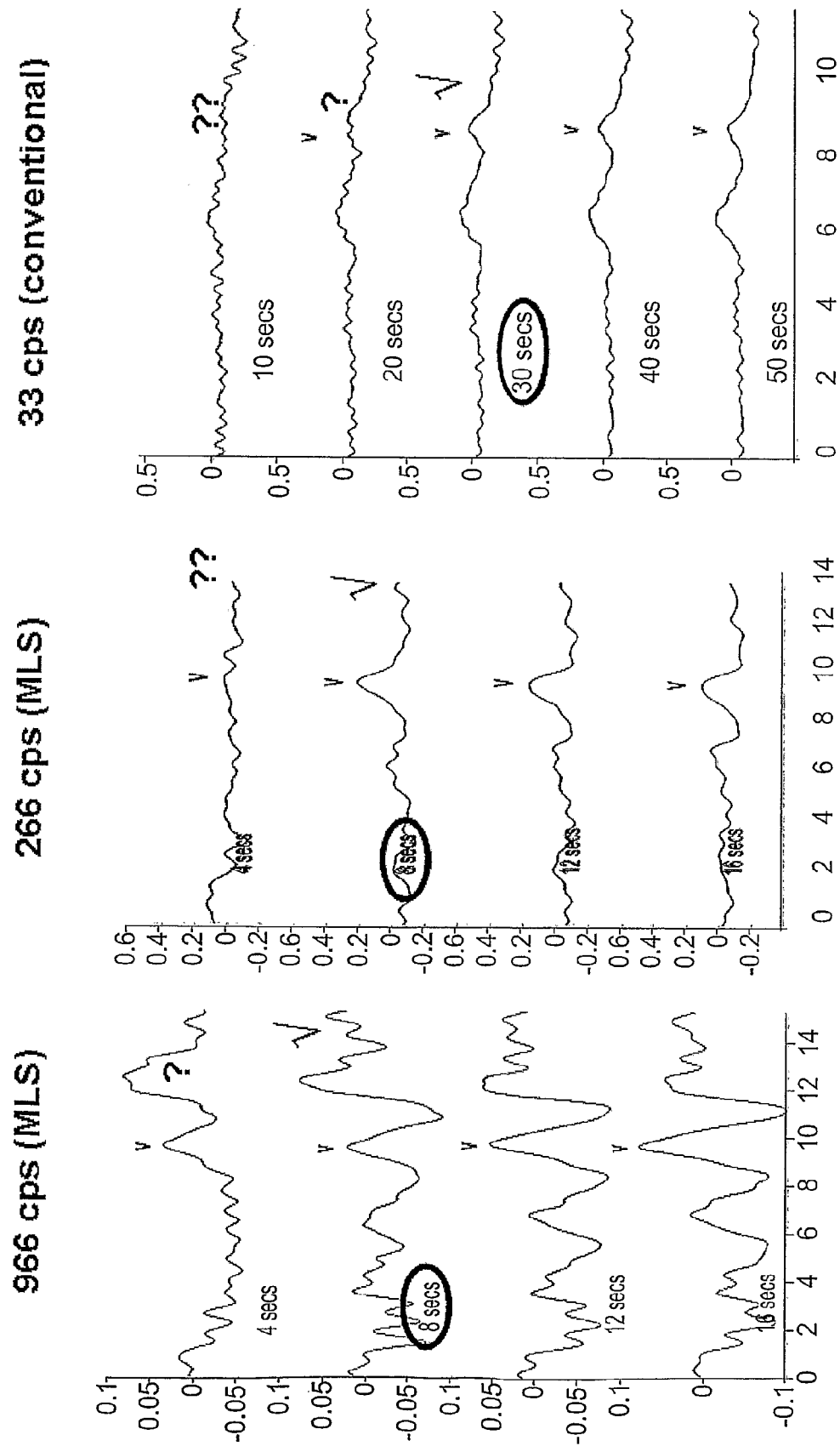
FIG. 15 demonstrates the efficacy of an embodiment of the invention in reconstructing an ABR for a neonate subject under different conditions to FIG. 14.

Similarly, FIG. 15 demonstrates the efficacy of the current invention when reconstructing an ABR acquired from a neonate at a stimulus intensity of 35 dBnHL. Response data was acquired at an average inter-stimulus interval of both 1.035 and 3.76 ms with a 100 μs click stimulus. The proposed reconstruction algorithm shows a clear decrease in the time required for an Audiologist to reliably detect the presence of wave V compared to the conventional periodic click stimuli presented at a (fixed) 30.3 ms inter-stimulus interval (8 seconds compared to 30 seconds).

In a further embodiment of the current invention the functional relationships shown in FIG. 3 and FIG. 4 can be estimated from ABR waves other than wave V. This is particularly convenient when estimating the hearing threshold of dogs, horses and other animals where the early ABR waves (I, II and III) are significantly larger than in humans. In addition, the relationship between ISI and wave amplitude/latency shown in FIG. 3 and FIG. 4 may also be estimated by combining the measurements from a number of different ABR waves, for example waves I, III and V. This is conveniently done by expressing the measured wave amplitudes and latencies as a percentage of their value at some common ISI such as 33 ms and then estimating overall changes in wave latency and amplitude from a weighted average of all measured waves. Alternatively, the relative latency of each ABR waveform can be estimated from the relative lag that produces the maximum cross-correlation between each pair of ABR waveforms collected at differing ISIs and relative amplitude can be estimated from the root mean square (RMS) value of the waveforms.

The invention is particularly efficient when applied to the recovery of ABR waveforms, however, there are a number of other related electrophysiological measurements to which the current invention can be successfully applied. In particular, the invention will also provide advantages in MLR compared to Bell et al and TEOAE compared to Thornton (both described above). The inventor also speculates that the invention may be applied to other stimuli-evoked responses such as responses to visual stimuli and tactile stimuli. For example, improved acquisition of response will be achieved in visually evoked potentials such as electroretinogram (ERG), sensory and motor nerve evoked potentials such as electroneurogram (ENG) and reflex evoked electromyography (EMG), and other auditory evoked potentials such as auditory late response (ALR).

The present invention therefore enables acquisition of an improved ABR or other physiological response. Embodiments of the present invention enable ABR waveforms to be acquired in a significantly reduced time compared to the prior art. That can improve the effectiveness of A-ABR devices in various ways. For example, according to a method of the present invention, a single stimulus intensity can be tested in significantly less time than is required using prior art techniques, allowing for more successful testing in difficult environments, such as where the test subject is a fidgety neonate or where there is significant background noise. Also, embodiments of the present invention enable multiple stimulus intensities to be tested during a test period that is comparable in length to prior art test periods, but that results in increased test accuracy and reliability.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this invention is intended to embrace all alternatives, modifications and variations of the present invention that have been discussed herein, and other embodiments that fall within the spirit and scope of the above described invention.

The invention claimed is:

1. A method for acquiring a physiological response, the method being performed by an automated auditory brainstem response (A-ABR) hardware apparatus and comprising the steps of:
presenting to a test subject, by the A-ABR hardware apparatus, a plurality of stimuli with variable inter-stimulus intervals;
detecting, by the A-ABR hardware apparatus, an electrophysiological signal from the test subject in response to the stimuli;
generating, by the A-ABR hardware apparatus, a recovery signal based on the stimuli, where an amplitude and latency of the recovery signal are modified according to the inter-stimulus intervals of the stimuli; and
determining, by the A-ABR hardware apparatus, a physiological response signal using both the electrophysiological signal and the recovery signal.

2. The method of claim 1 wherein the stimuli are presented cyclically.

3. The method of claim 1 wherein the plurality of stimuli is in excess of 1,000 auditory stimuli presented to the test subject's ear.

4. The method of claim 1 wherein the stimuli are auditory stimuli and the physiological response is an auditory brainstem response (ABR).

5. The method of claim 1 wherein the auditory stimuli are selected from one of: broad band clicks; tone bursts; noise bursts; or chirp stimuli.

6. The method of claim 1 wherein the plurality of stimuli is a Maximum Length Sequence and the length of the sequence is longer than the expected length of the electrophysiological signal.

7. The method of claim 1 wherein generating a recovery signal based on the auditory stimuli comprises application of a comb filter.

8. The method of claim 1 wherein the step of generating a recovery signal produces a unipolar recovery sequence.

9. The method of claim 1 wherein the step of generating a recovery signal produces a bipolar recovery sequence.

10. The method of claim 1 wherein the step of generating a recovery signal further includes the step of determining the amplitude and latency by reference to functional relationships determined from a control group with known physiological response.

11. The method of claim 1 wherein the step of determining a physiological response signal includes performing artefact detection to remove signals contaminated by artefacts.

12. The method of claim 1 wherein the step of determining a physiological response signal includes calculating an ensemble average of signals.

13. The method of claim 12 further including the step of cross-correlating the ensemble average with the recovery signal to obtain the physiological response.

14. The method of claim 1 wherein the method is applied to both ears of a single test subject simultaneously.

15. The method of claim 14 wherein the plurality of stimuli is a Maximum Length Sequence and the length of the sequence is longer than twice the expected length of the electrophysiological signal.

16. The method of claim 1 wherein the test subject is a human neonate.

17. The method of claim 1 wherein the plurality of stimuli are visual stimuli.

18. The method of claim 17 wherein the electrophysiological signal is detected as an electroretinogram.

19. The method of claim 1 wherein the plurality of stimuli are tactile stimuli.

20. The method of claim 19 wherein the electrophysiological signal is detected by reflex evoked electromyography.

21. The method of claim 1 further including the step of adjusting the inter-stimulus intervals of the plurality of stimuli so that the detected electrophysiological signal simulates a signal from a linear system.

22. The method of claim 21 wherein the amplitude and latency of the recovery signal are unmodified.

23. An apparatus for acquiring a physiological response, the apparatus comprising:
a sound transducer that receives a plurality of stimuli with variable inter-stimulus intervals and is configured to present the stimuli to a test subject;
electrodes that detect an electrophysiological signal from the test subject in response to the stimuli;
wherein the apparatus is configured to:
generate a recovery signal based on the stimuli, where an amplitude and latency of the recovery signal are modified according to the inter-stimulus intervals of the stimuli; and
determine a physiological response signal using both the electrophysiological signal and the recovery signal.

24. The apparatus of claim 23, further comprising a processor in which the recovery signal is generated and the physiological response is determined.

25. The apparatus of claim 23, further comprising an amplifier coupled to the sound transducer, the amplifier and sound transducer being calibrated to present the stimuli at predetermined intensity levels.

26. The apparatus of claim 23, further comprising a biomedical amplifier coupled to the electrodes to acquire the electrophysiological signal from the electrodes.

27. A method for acquiring a physiological response, the method comprising:
presenting to a test subject, by a sound transducer, a plurality of stimuli with variable inter-stimulus intervals;
detecting, using electrodes, an electrophysiological signal from the test subject in response to the stimuli;
generating a recovery signal based on the stimuli, where an amplitude and latency of the recovery signal are modified according to the inter-stimulus intervals of the stimuli; and
determining a physiological response signal using both the electrophysiological signal and the recovery signal.

28. The method of claim 27 wherein the stimuli are presented cyclically.

29. The method of claim 27 wherein the plurality of stimuli is in excess of 1,000 auditory stimuli presented to the test subject's ear.

30. The method of claim 27 wherein the stimuli are auditory stimuli and the physiological response is an auditory brainstem response (ABR).

31. The method of claim 27 wherein the auditory stimuli are selected from one of: broad band clicks; tone bursts; noise bursts; or chirp stimuli.

32. The method of claim 27 wherein the plurality of stimuli is a Maximum Length Sequence and the length of the sequence is longer than the expected length of the electrophysiological signal.

33. The method of claim 27 wherein generating a recovery signal based on the auditory stimuli comprises application of a comb filter.

34. The method of claim 27 wherein the step of generating a recovery signal produces a unipolar recovery sequence.

35. The method of claim 27 wherein the step of generating a recovery signal produces a bipolar recovery sequence.

36. The method of claim 27 wherein the step of generating a recovery signal further includes the step of determining the amplitude and latency by reference to functional relationships determined from a control group with known physiological response.

37. The method of claim 27 wherein the step of determining a physiological response signal includes performing artefact detection to remove signals contaminated by artefacts.

38. The method of claim 27 wherein the step of determining a physiological response signal includes calculating an ensemble average of signals.

39. The method of claim 38 further including the step of cross-correlating the ensemble average with the recovery signal to obtain the physiological response.

40. The method of claim 27 wherein the method is applied to both ears of a single test subject simultaneously.

41. The method of claim 40 wherein the plurality of stimuli is a Maximum Length Sequence and the length of the sequence is longer than twice the expected length of the electrophysiological signal.

42. The method of claim 27 wherein the test subject is a human neonate.

43. The method of claim 27 wherein the method is performed using an automated auditory brainstem response (A-ABR) device.

44. The method of claim 27 wherein the plurality of stimuli are visual stimuli.

45. The method of claim 44 wherein the electrophysiological signal is detected as an electroretinogram.

46. The method of claim 27 wherein the plurality of stimuli are tactile stimuli.

47. The method of claim 46 wherein the electrophysiological signal is detected by reflex evoked electromyography.

48. The method of claim 27 further including the step of adjusting the inter-stimulus intervals of the plurality of stimuli so that the detected electrophysiological signal simulates a signal from a linear system.

49. The method of claim 48 wherein the amplitude and latency of the recovery signal are unmodified.

\* \* \* \* \*